(12) United States Patent
Guo et al.

(10) Patent No.: US 11,957,326 B2
(45) Date of Patent: Apr. 16, 2024

(54) VARIABLE LENGTH TELESCOPING APPLICATION TIPS FOR FLOWABLE HEMOSTATS AND SEALANTS APPLICATION

(71) Applicant: Ethicon, Inc., Raritan, NJ (US)

(72) Inventors: Jianxin Guo, Raritan, NJ (US); Sridevi N. Dhanaraj, Raritan, NJ (US); Leo Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 0 days.

(21) Appl. No.: 17/723,984

(22) Filed: Apr. 19, 2022

(65) Prior Publication Data

US 2023/0329686 A1 Oct. 19, 2023

(51) Int. Cl.
*A61B 17/00* (2006.01)

(52) U.S. Cl.
CPC ........ *A61B 17/00491* (2013.01); *A61B 2017/00495* (2013.01); *A61B 2017/00522* (2013.01)

(58) Field of Classification Search
CPC ........ A61B 17/00491; A61B 17/00234; A61B 17/0218; A61B 17/0485; A61B 17/22031; A61B 17/3421; A61B 17/3439; A61B 17/3478; A61B 2017/00494; A61B 2017/00522; A61B 2017/00473; A61B 2017/00867; A61B 2017/06104; A61B 2017/22035; A61B 2017/2212; A61B 2017/3405; A61B 2017/3443; A61B 1/00087; A61B 1/00154; A61B 1/053; A61B 1/3132; A61B 1/32; A61B 2034/30; A61B 2090/034; A61B 90/361
See application file for complete search history.

(56) References Cited

U.S. PATENT DOCUMENTS

| | | | |
|---|---|---|---|
| 5,324,258 A | 6/1994 | Rohrbough | |
| 5,799,835 A * | 9/1998 | Gobbel | B05B 15/628 239/281 |
| 6,585,701 B1 | 7/2003 | Dysarz | |
| 6,884,230 B1 | 4/2005 | Epstein et al. | |

(Continued)

FOREIGN PATENT DOCUMENTS

| | | |
|---|---|---|
| EP | 0543499 A1 | 5/1993 |
| EP | 2506893 A2 | 10/2012 |

(Continued)

OTHER PUBLICATIONS

International Search Report dated Jul. 12, 2023 for Application No. PCT/IB2023/053757.

*Primary Examiner* — Mohamed G Gabr

(74) *Attorney, Agent, or Firm* — David R. Crichton; Leo B. Kriksunov

(57) ABSTRACT

The present invention is directed to a variable length applicator system for delivery of at least one medically useful liquid, comprising an elongated, telescopically extendable, variable length cannula having a liquid pump containing said liquid connected to said cannula at a proximal end, and a spray nozzle mounted on said cannula at a distal end; a coiled and extendable tubular conduit connected to and in fluid communication with, both said liquid pump and said spray nozzle; wherein an axial extension of said cannula is configured to cause a matching axial extension of said coiled tubular conduit.

18 Claims, 12 Drawing Sheets

(56) References Cited

U.S. PATENT DOCUMENTS

| | | | |
|---|---|---|---|
| 8,372,092 | B2 | 2/2013 | Gabel et al. |
| 9,597,463 | B2 | 3/2017 | Li et al. |
| 9,744,548 | B2 | 8/2017 | Gopalarao et al. |
| 10,390,694 | B2 | 8/2019 | Farin et al. |
| 10,952,709 | B2 | 3/2021 | D'alessio |
| 2002/0165337 | A1* | 11/2002 | Wallace ................ A61L 27/52 528/499 |
| 2010/0206905 | A1 | 8/2010 | Horner et al. |
| 2013/0281918 | A1 | 10/2013 | Koichi |
| 2014/0005474 | A1* | 1/2014 | Farin ................ A61B 1/3132 600/104 |
| 2016/0236224 | A1* | 8/2016 | Gopalarao ............ B05B 12/002 |
| 2017/0100115 | A1* | 4/2017 | Mathys ............ A61B 17/00491 |
| 2017/0304562 | A1 | 10/2017 | Riebman et al. |

FOREIGN PATENT DOCUMENTS

| | | |
|---|---|---|
| EP | 2797649 B1 | 2/2017 |
| JP | 2016054853 A | 4/2016 |

\* cited by examiner

VARIABLE LENGTH TELESCOPING APPLICATION TIPS FOR FLOWABLE HEMOSTATS AND SEALANTS APPLICATION

FIELD OF THE INVENTION

The present invention relates to an applicator and method of applying liquid and or flowable medicants to biological tissue, particularly for sealing leaks from tissue and tissue wounds (e.g. fluid, air), tissue fixation (e.g. graft fixation), hemostasis, and therapeutic treatments, and is particularly useful for applying medicants by a spray from a hand-held or robotic applicator. The invention further relates to applicators and/or tips that have a variable length that can be changed as needed for delivery during different procedures such as thoracic surgery and laparoscopic abdomen surgery, where the length requirements are different. The length can also be changed as needed in open procedure or in minimally invasive procedures through a trocar so that the distance from the applicator to the surface of tissue can be adjusted or selected by telescopically extending/lengthening or contracting/shortening the applicator tip.

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. The control of bleeding is essential and critical in surgical procedures to minimize blood loss, to reduce post-surgical complications, and to shorten the duration of the surgery in the operating room. Surgeons use tissue sealants in a wide range of different clinical applications. Sealants can be used as both a primary and/or secondary method of joining or sealing tissue. Various technologies have been developed for the formulation of tissue adhesives. Some of them are of synthetic origin, such as the glues based on cyanoacrylates (2-butyl cyanoacrylate, 2-octyl cyanoacrylate), or on synthetic polymers (polyurethanes, polymethylmethacrylates) and others contain biological materials such as collagen or fibrin.

A common class of tissue adhesives is fibrin-based and contains a concentrate of fibrinogen and thrombin. Fibrin adhesives are typically two-component adhesives that when mixed together react to simulate the last stages of the coagulation cascade. The resulting clot adheres to tissue and bridges a gap between the tissues until healing can occur.

Sealants, adhesives, or glues based on albumin or gelatin cross-linked with an aldehyde are also known. Representative of this class of glues are gelatin-resorcinol cross-linked with formaldehyde or glutaraldehyde. Gelatin-based glues have been extensively studied and shown to generally be effective. Cyanoacrylates, polyurethanes, polymethylmethacrylates, among other synthetic polymers, have been also investigated as tissue glues.

As stated above, known hemostatic and sealant materials include absorbable liquid sealants such as fibrin sealants which are formed from blood plasma components and comprise a first agent containing fibrinogen and a second agent which usually includes thrombin. Fibrinogen is capable of a polymerizing to form a solid fibrin clot when the agents are mixed.

Also known are sealants incorporating multi-arm reactive polyethylene glycol polymers having at least 2, more preferably 4 or more reactive groups, such as electrophilic or nucleophilic groups. Such PEG-based absorbable liquid sealants utilizing multi-arm PEG molecules typically have reactive groups such as PEG-SG or PEG-NETS, optionally in combination with buffers, PEG-amines, albumin, and similar compounds.

Other hemostatic materials for controlling excessive bleeding include Topical Absorbable Hemostats (TAHs) which are widely used in surgical applications. TAHs encompass products based on oxidized cellulose (OC), oxidized regenerated cellulose (ORC), gelatin, collagen, chitin, chitosan, etc. These materials can be delivered in solid form, as scaffolds, as suspensions or paste, or as powders.

Application of any medicants, including biological sealants, to target areas, requires accurate mixing and targeting, particularly when a multi-part sealant is used, due to the rapid polymerization upon interaction of the components. For delivery of fibrin sealant, for example, the two components are typically dispensed simultaneously from separate devices, such as syringes, and mixed together immediately prior to application or on the tissue surface.

Maintaining optimal distances from the dispensing nozzle to the treated areas of tissue during dispensing of the tissue sealants and hemostats is important for targeting, optimal mixing of the components, optimal spray patterns, and, especially but not only in cases of gas-assisted delivery, for avoiding gas embolisms. Maintaining optimal distances is especially important during laparoscopic or minimally invasive delivery.

European Patent Application EP2506893A2 titled "ADHESIVE DELIVERY DEVICES, SYSTEMS AND METHODS", discloses an adhesive material injection system for delivering adhesive to a patient site comprising: adhesive material; and a delivery device comprising: a housing; and a nozzle, said nozzle comprising a proximal end and a distal end wherein the adhesive material is configured to exit said nozzle distal end.

U.S. Pat. No. 8,372,092B2 titled "Applicator instruments having protective carriers for hemostats and methods therefor" discloses an instrument for controlling bleeding comprising: an outer shaft having a proximal end, a distal end, and a central lumen extending to the distal end thereof; an intermediate shaft telescopically received within the central lumen of said outer shaft, said intermediate shaft having a proximal end, a distal end, and a central lumen extending to the distal end thereof; a first actuator coupled with said outer shaft for sliding said outer shaft axially relative to said intermediate shaft; an inner shaft telescopically received within the central lumen of said intermediate shaft, said inner shaft having a proximal end and a distal end that extends distally from said intermediate shaft; a hemostat disposed distal to the distal end of said inner shaft and distal to the distal end of said outer shaft; a fluid-resistant element connected to and extending distally from the distal end of said outer shaft and surrounding said hemostat, wherein said fluid-resistant element comprises a breakable, fluid-resistant seal at a distal end thereof, and wherein said outer shaft and said fluid-resistant element connected to the distal end of said outer shaft slide together, axially toward the proximal end of said instrument and relative to said intermediate shaft, said inner shaft and said hemostat for passing said hemostat through said fluid-resistant seal.

U.S. patent Ser. No. 10/390,694B2 tilted "Micro laparoscopy devices and deployments thereof" discloses a guiding cannula comprising: an inner sleeve having a proximal end and a distal end; an outer sleeve slidably receiving the inner sleeve; a lumen extending axially between a distal opening and a proximal opening, wherein the lumen is configured to receive a laparoscopic device from the distal opening and/or the proximal opening; a sealing member configured to seal the lumen, wherein the sealing member is fixed relative to the outer sleeve, and the inner sleeve is movable relative to the sealing member; a handle fixed to the proximal end of the inner sleeve; and a conic body connected to the distal end of the inner sleeve, wherein the conic body defines an edge along a single plane for guiding the laparoscopic device into the lumen, and the edge is continuous in a contracted configuration and an extended configuration, wherein the outer sleeve defines an outer diameter adapted to fit in a port lumen of a laparoscopic port having a port seal, said guiding cannula is configured to reversely deactivate said port seal when introduced through the laparoscopic port, said guiding cannula is telescopically extendible to receive the laparoscopic device in said laparoscopic port, and said sealing member is configured to receive said laparoscopic device while sealing said lumen from an outside environment.

U.S. Pat. No. 9,744,548B2 titled: Telescoping spray wand assembly" discloses a telescoping wand assembly for use in dispensing liquid from a container, comprising: a) a trigger module extending along a longitudinal axis between proximal and distal ends and comprising a tubular handle member, a user accessible trigger positioned externally of said tubular handle member and selectively movable between first and second positions, a hose positioned within said tubular handle member and adapted to transport liquid from the container, and a valve actuating member that is selectively, movably actuable by movement of said trigger between its first and second positions; b) a tube assembly interconnected to said handle member c) a first tube interconnected to said handle member and comprising opposing first and second ends and a predetermined internal cross-sectional dimension; d) a second tube positioned co-axially within said first tube and in fluid communication with said hose and comprising first and second ends and a predetermined external cross-sectional dimension, wherein said predetermined external cross-sectional dimension is less than said predetermined internal cross-sectional dimension of said first tube with a cross-sectional gap defined there between; e) a third tube coupled in sealed relation to and in fluid communication with said second tube wherein said third tube is selectively slidably movable along said longitudinal axis towards and away from said trigger module; f) a nozzle in fluid communication with said third tube; and g) a valve mechanically linked to said first tube and positioned between said third tube and said nozzle and in spring biased relation to said nozzle for selective movement between a first position wherein said nozzle is sealed relative to said third tube and a second position wherein said nozzle is in fluid communication with said third tube, whereby selective movement of said trigger between its first and second positions causes said first tube to longitudinally move which in turn causes said valve to move between its first and second positions, respectively.

U.S. Patent Application Publication No. 2017/0100115A1 titled "LAPAROSCOPIC SPRAY APPLICATOR AND ADAPTER", discloses an applicator for spraying at least two components in the interior of the body of a patient by using a compressed gas, comprising: a connecting piece for connecting the applicator to reservoirs for the components and for feeding a compressed gas to the applicator; a multi-lumen tube which defines a central longitudinal axis, with a proximal end, which is connected to the connecting piece, and with a distal end; a spray head which is located at the distal end of the multi-lumen tube, and at least one first flexible wire which is arranged in a first lumen of the multi-lumen tube; and at least one adapter which is arranged at the proximal or distal end of the multi-lumen tube in order to connect the multi-lumen tube to the connecting piece or to the spray head, wherein the adapter comprises two tube connectors which are introduced into a second and a third lumen of the multi-lumen tube, wherein the second and the third lumen extend off-center with respect to the longitudinal axis, and wherein the first lumen, in which the first flexible wire is arranged, likewise extends off-center with respect to the longitudinal axis and offset from the second and the third lumen in the circumferential direction.

U.S. Patent Application Publication No. 2010/0206905A1 titled "DUAL FLUID DISPENSER" discloses a self-contained dual fluid dispenser for storing and dispensing two fluids, comprising: a dual fluid container having an outer cartridge wall and a first outlet; a delivery tube disposed at least partially within the outer cartridge wall and including a second outlet; a first piston disposed between the outer cartridge wall and the delivery tube, the first piston forming a first fluid chamber for a first fluid; a neck connected with the outer cartridge wall and adapted to be coupled to an applicator; a second piston disposed at least partially within the neck and coupled with a side wall defining a second fluid chamber for a second fluid wherein the side wall slides within the neck in a telescoping manner and also slides over the delivery tube in a telescoping manner; and a transmission structure operative to transmit force from the second piston to the first piston to thereby dispense the first and second fluids from the first and second outlets.

U.S. patent Ser. No. 10/952,709B2 titled "Extended tip spray applicator for two-component surgical sealant, and methods of use thereof" discloses a tip assembly, comprising a proximal end, comprising a Y fitting, the Y fitting comprising a first proximal end; a second proximal end, the first and second proximal ends connected to an applicator; a distal end; a first fluid channel extending from the first proximal end to the distal end, the first fluid channel including a first section and a second section perpendicular to the first section; and a second fluid channel extending from the second proximal end to the distal end, the second fluid channel including a third section and a fourth section perpendicular to the third section; a distal end; a mixing nozzle, comprising a proximal end, comprising a fluid inlet; a distal end, comprising a fluid outlet, wherein the distal end of the mixing nozzle corresponds to the distal end of the tip assembly; and a mixing chamber disposed between and in fluid communication with the fluid inlet and the fluid outlet; a tube extending from the distal end of the Y fitting to the proximal end of the mixing nozzle, the tube defining a tube cross section; a first cannula, disposed within and extending along substantially the entire length of the tube, in fluid communication with the first fluid channel of the Y fitting and the fluid inlet of the mixing nozzle, the first cannula being perpendicular to the second section of the first channel, the first cannula defining a first cross section; a second cannula, disposed within and extending along substantially the entire length of the tube, in fluid communication with the second fluid channel of the Y fitting and the fluid inlet of the mixing nozzle, the second cannula being perpendicular to the fourth section of the second channel, the second cannula defining a second cross section, and a third fluid channel extending from a proximal inlet of the Y fitting to a distal outlet in fluid communication with the mixing chamber of the mixing nozzle, the third fluid channel having a third cross section, wherein the third cross section is equal to the tube cross section minus the first and second cross sections, the third fluid channel being in fluid communication with a built-in gas pump of the applicator, wherein the tube, the first cannula, and the second cannula are flexible.

U.S. Pat. No. 9,597,463B2 titled "Injection devices with controllable depth adjustability and methods of use discloses an injection device, comprising: a sheath having a distal end; an injector having an outlet tube movably positioned within the sheath and including a distal portion with a penetrating tip, wherein in a first state, the tip is located a first distance relative to the distal end of the sheath, and in a second state, the tip is located a second distance relative to the distal end of the sheath; and an adjuster contacting the sheath and having a first orientation and a second orientation different than the first orientation, wherein in the first orientation the adjustor extends radially inwardly into the injector a first distance enabling movement of the tip between the first state and the second state, and in the second orientation the adjustor extends radially inwardly into the injector a second distance, different than the first distance, thereby compressing the sheath about the outlet tube and preventing movement of the tip between the first state and the second state.

U.S. Pat. No. 6,585,701B1 titled "Trap in modular hub chamber spring needle cannula", discloses a modular needle assembly for use with a conventional syringe, comprising: (a) a hub chamber comprising a first end having a hub tunnel therethrough and a second end having a hub for connecting to the conventional syringe; (b) a biased spring needle cannula having a distal end extending through the hub tunnel and a proximal end fixed to the hub for the transfer of medicament from the syringe; (c) a latch formed on the inside of the hub chamber preventing the distal end of the needle cannula from being pulled into the hub chamber; and (d) a latch release button extending through a hole in the hub chamber near the latch for disengaging the latching means.

There is a need in a variable length sealant applicator or spray systems that can extended or shortened telescopically based on the application route, facilitating use in open and minimally invasive or laparoscopic procedures, with the distance from the applicator to spray tip adjustable to facilitate sealant application or spray at an optimal distance from tissue. More specifically, there is a need in applicator tip that can be telescopically lengthened for use when applied though a trocar and mutatis mutandis shortened for use when applied in open procedure directly on tissue. Further, patient size differences may necessitate a need in variable length applicator tip in either open procedure or in a minimally invasive or laparoscopic procedure.

There is an unmet need in liquid and or flowable sealant or hemostat dispensing/spraying devices that are ensuring that applicator tip can be positioned at optimal distances from tissue.

SUMMARY OF THE INVENTION

In one aspect, a variable length applicator system or spay system for delivery of at least one medically useful flowable material, such as liquid, comprises an elongated, telescopically extendable, variable length cannula having a liquid pump containing said liquid connected to said cannula at a proximal end, and a spray nozzle mounted on said cannula at a distal end; a coiled and extendable tubular conduit connected to and in fluid communication with, both said liquid pump and said spray nozzle; wherein an axial extension of said cannula is configured to cause a matching axial extension of said coiled tubular conduit.

In some embodiments, the pump comprises a dual barrel syringe containing a first liquid in a first barrel and a second liquid in a second barrel, with the first and second liquids containing reagents that are reactive upon mixing. The liquids here are defined as flowable materials, that are expressible from a syringe. Such flowable materials can have a viscosity of about 1 to 1000 cps (centipoise) at 20 C, or preferably less than 200 cps, or less than 1000 cps, or less than 10,000 cps. In some embodiments these flowable and or liquid materials can be more viscous, having a honey-like consistency, with viscosity of about 1000-10,000 cps or even higher viscosities characteristic of a viscous paste, such as viscosities in the ranges of 10,000-250,000.

In some embodiments, the cannula comprises a plurality of hollow tubular segments that are axially aligned and slidably inserted into one another, forming outer and inner segments, with cannula configured to slidably axially telescopically extend when inner segments are axially pulled from outer segments and to slidably axially telescopically contract when said inner segments axially slide back into said outer segments.

In some embodiments, the cannula is hollow and the coiled conduit is positioned inside the cannula. In some embodiments, the coiled conduit is positioned outside the cannula and is wrapped around the cannula.

In another aspect, the invention is directed to a method of using the applicator system comprising the steps of: directing the spray nozzle towards a target; telescopically extending or contracting said cannula towards said target or from said target until an optimal spraying distance between said target and said spray nozzle is reached; actuating said liquid pump causing expression of said liquid onto said target.

BRIEF DESCRIPTION OF THE FIGURES

FIG. 1 shows a schematic side cross-sectional view of an embodiment of delivery device or applicator system of the present invention.

FIG. 2 shows a schematic side cross-sectional view of an embodiment of delivery device or applicator system of the present invention.

FIG. 3 shows a schematic side cross-sectional view of an embodiment of delivery device or applicator system of the present invention.

FIG. 4 shows a perspective view of an embodiment of the present invention.

FIG. 5 shows a side partial cross-section view of an embodiment of delivery device or applicator system of the present invention.

FIG. 6 shows a side partial cross-sectional view of an embodiment of delivery device or applicator system of the present invention.

FIG. 7 shows a side view of a portion of an embodiment of delivery device or applicator system of the present invention.

FIG. 8 shows a side partial cross-section view of a portion of an embodiment of delivery device or applicator system of the present invention.

FIG. 9 shows an exploded view of a portion of an embodiment of delivery device or applicator system of the present invention.

FIG. 10 shows a photo of a perspective view of an embodiment of delivery device or applicator system of the present invention.

FIG. 11 shows a photo of a perspective view of an embodiment of delivery device or applicator system of the present invention.

DETAILED DESCRIPTION OF THE INVENTION

Briefly, an applicator system for spraying a tissue treatment medicant onto a tissue comprises a variable length sealant applicator, that can be extended or shortened telescopically based on the application route, facilitating use in open surgery and also and in minimally invasive or laparoscopic procedures, with the distance from the pump to spray tip or mixing tip or expression tip adjustable to facilitate spray at an optimal distance from tissue. The inventive applicator cannula can be telescopically lengthened for use such as when applied though a trocar and mutatis mutandis shortened for use such as when applied in open surgical procedure directly on tissue or vice versa. In embodiments, liquid sealant or hemostat dispensing/spraying device enables spray nozzle positioned at optimal distances from tissue, with telescopic extension of applicator cannula avoiding spraying from a very large and non-optimal distance during minimally invasive or laparoscopic procedures thus providing for good targeting and narrow spray spot. The embodiments of the present invention are also especially suitable for robotic surgery and robot-assisted surgery, as well as for video-assisted thoracic surgery.

Figures 1, 2, 3:
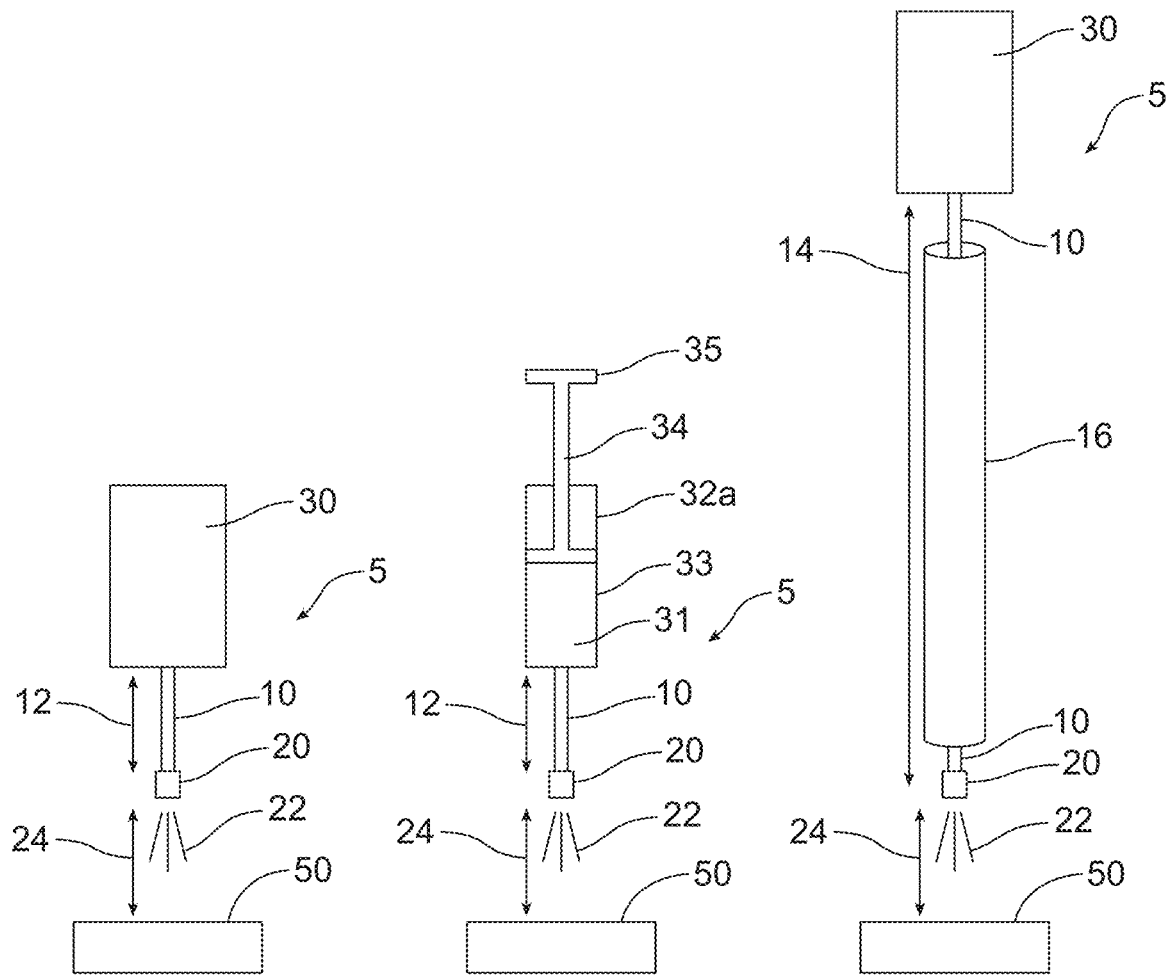

Referring to FIG. 1, a schematic side cross-sectional view of delivery device or applicator system 5 is presented, delivering medically useful liquid, such as sealant spay 22 onto tissue 50 from spray nozzle, spray exit port, expression port, or spray mixing tip 20, with spray nozzle 20 to tissue distance 24 being selected so as to deliver at an optimal distance for tissue 50 coverage and targeting. Spray nozzle 20 is supplied with liquid sealant through a variable length hollow cannula 10, which in turn receives liquid sealant from liquid sealant pump 30. Cannula 10 is variable length telescopic cannula, being reversibly axially extendable, configured for axial elongation and shortening, or axial extending and contracting its length as needed based on the procedure and distance to tissue 50. As shown, in some applications, such as in an open surgery, the configuration of applicator system 5 and cannula 10 is in a non-extended state, in other words, in a contracted state, with non-extended length 12 of cannula 10 shown in FIG. 1.

Liquid sealant pump 30 can be of any construction known to a skilled artisan, including manually or electrically or mechanically or hydrostatic or gas pressure driven pump, including hand-operated pumps and syringes and motorized liquid pumps. In an embodiment depicted in FIG. 2, pump is shown as a manually operated syringe, such as dual barrel syringe or single barrel syringe. Referring to FIG. 2, liquid sealant pump is shown as a conventional single barrel syringe 32a having barrel 33 containing liquid 31, with plunger 34 having handle 35 facilitating expression of liquid 31 into conduits (not shown) inside cannula 10 and then into exit port 20. Exit port 20 is in fluid communication with syringe barrel 33 through conduits inside cannula 10 (shown in following Figures).

In some embodiments, single barrel syringe pump 30 is used to deliver one component to exit port 20 for treating tissue 50. In the preferred embodiments, a dual barrel syringe pump 32, as will be shown in following Figures, is configured for delivering two reactive components to spray mixing tip 20, with two reactive components mixing inside spray mixing tip or exit port 20 and exiting port 20 as a mixture. In some embodiments, dual barrel syringe pump 30 is configured for delivering two reactive components to spray exit port 20, which in this embodiment is configured for spraying or dripping two components separately, without mixing inside port 20.

Referring to FIG. 3, a schematic side cross-sectional view of delivery device or applicator system 5 is presented, delivering liquid sealant spay 22 onto tissue 50 from spray nozzle 20 through a hollow body access port or trocar 16, with spray nozzle 20 to tissue distance 24 being selected so as to deliver at an optimal distance 24 for tissue coverage and targeting. At least a portion of cannula 10 is positioned inside trocar 16. As shown, in a minimally invasive or laparoscopic surgery configuration of applicator system 5, cannula 10 is in a telescopically extended or elongated state, with extended length 14 of cannula 10 shown in FIG. 3.

Figure 4:
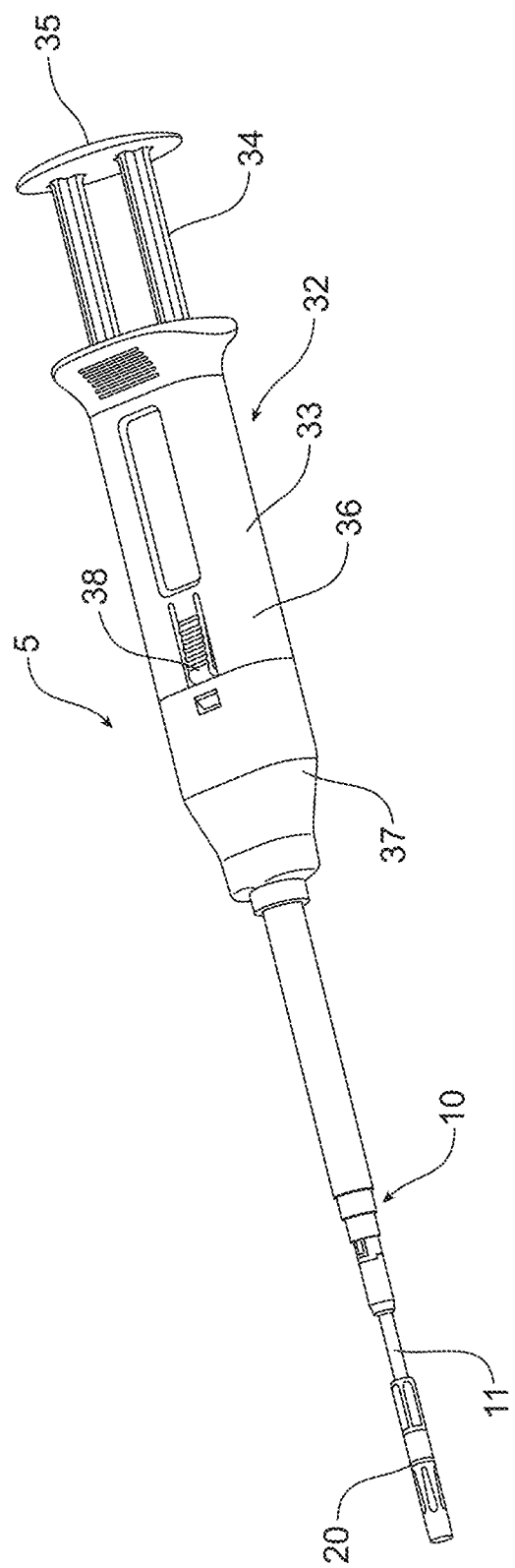

Referring to FIG. 4, a perspective view of an embodiment of the present invention is shown, with applicator system 5 comprising dual barrel syringe 32 having barrels 33 (not visible in FIG. 4) inside syringe housing 36, with dual plunger 34 having handle 35 also shown. Cannula 10 is terminating with spray and mixing nozzle 20; cannula 10 is shown connected to dual barrel syringe 32 at manifold housing 37. Manifold housing 37 is connected to syringe housing 36, optionally with connection secured by locking tab 38. Optional connector 11, which can be a malleable connector, can be interposed between cannula 10 and spray and mixing nozzle 20 to facilitate angular and sideways spraying if connector 11 is malleable. Applicator system 5 is shown with cannula 10 in a non-extended (contracted) state.

Figure 5:
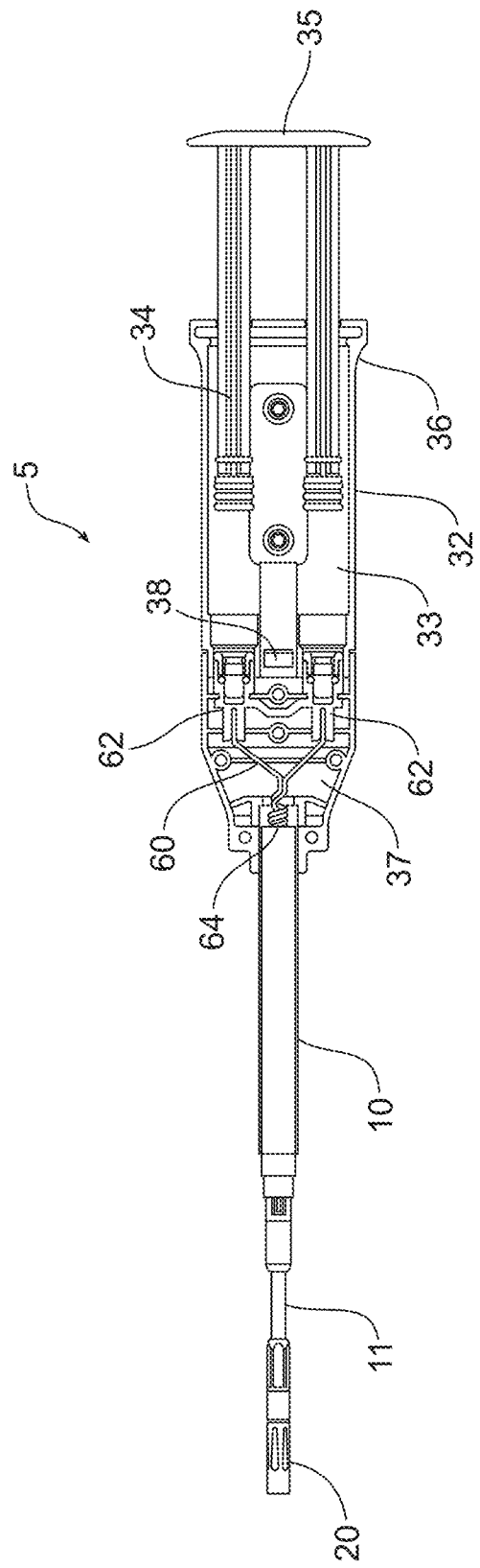
Figure 6:
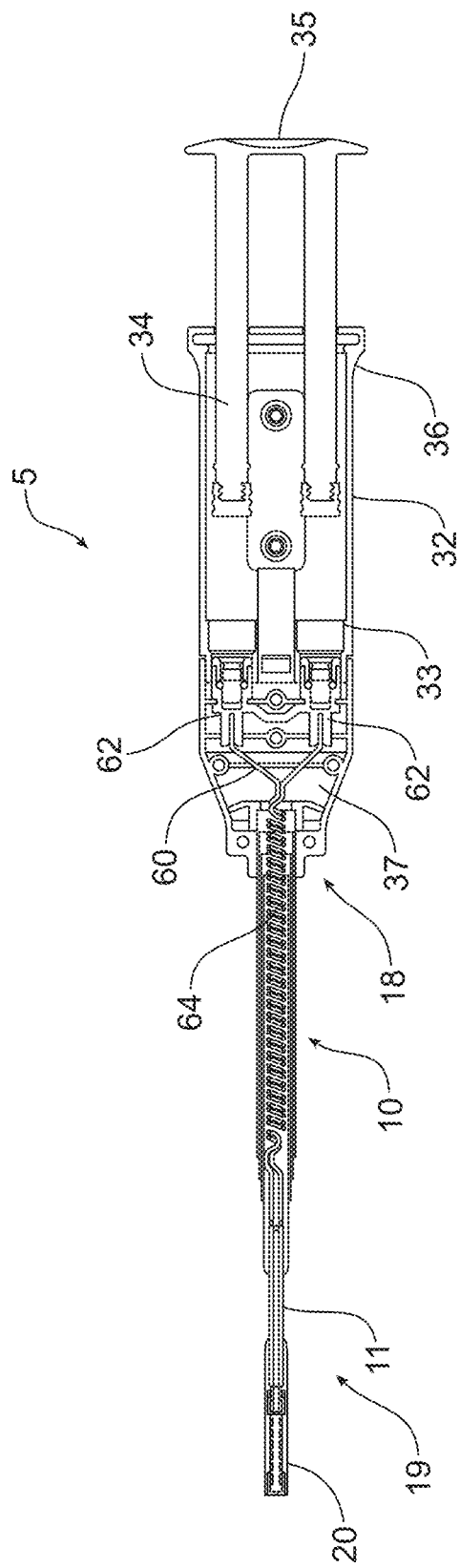

Referring to FIGS. 5 and 6, a side cross-sectional view of an embodiment of the present invention is shown, with applicator system 5 comprising dual barrel syringe 32 having barrels 33 situated inside syringe housing 36, with plungers 34 having handle 35 also shown. Applicator system 5 is shown with cannula 10 in a non-extended (contracted) state. Cannula 10 is connected to manifold housing 37 and syringe housing 36 at a proximal end 18 and is connected to nozzle 20 at a distal end 19, optionally via connector 11. Barrels 33 terminate in exit connectors 62 configured to establish fluid communication between barrels 33 and flexible component tubes 60. Component tubes 60 are flexible and run inside manifold housing 37 and enter hollow tubular cannula 10 in coiled state as coil 64. Coil 64 can comprise two separate coils running in parallel side by side or a double tube coil, or a double helix shaped coil of two separate tubes running together. In the embodiment shown, coil 64 comprises a coiled dual lumen tubing, which can be separated into two separate tubes for connection to exit connectors 62. The coiled nature of component tubes in coiled state as coil 64 enable substantial elongation of coil 64 inside hollow cannula 10 upon elongation of cannula 10.

Figure 7:
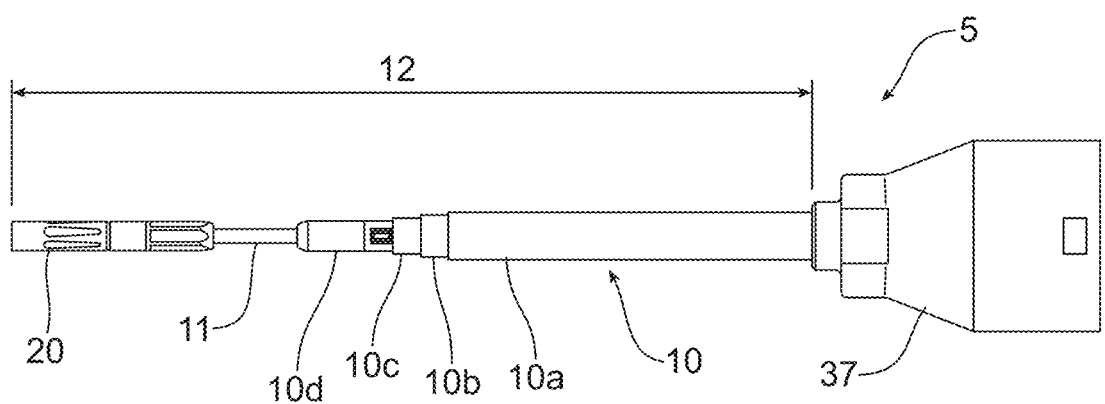

Referring to FIG. 7, a side view of an embodiment of the present invention is shown, with a portion of applicator system 5 showing manifold housing 37, cannula 10, and spray and mixing nozzle 20. Applicator system 5 is shown with cannula 10 in a non-extended (contracted) state, having length 12. Also shown is the detail of telescopic hollow cannula 10, which comprises of a plurality of hollow tubular segments, four as shown, tubes 10a, 10b, 10c, 10d axially aligned and slidably inserted into one another, and configured to slidably axially telescopically extend when inner tubes are axially pulled from outer tubes and configured to slidably axially telescopically contract when inner tubes side back inside outer tubes. As shown, tube 10a is external or outer tube or segment, and contains inner tubes 10b, 10c, 10d. Tube 10b is also external or outer to tube 10c, tube 10c is external or outer to 10d. Thus the same tubular segment can be simultaneously inner and outer segment with respect to other segments.

Figure 8:
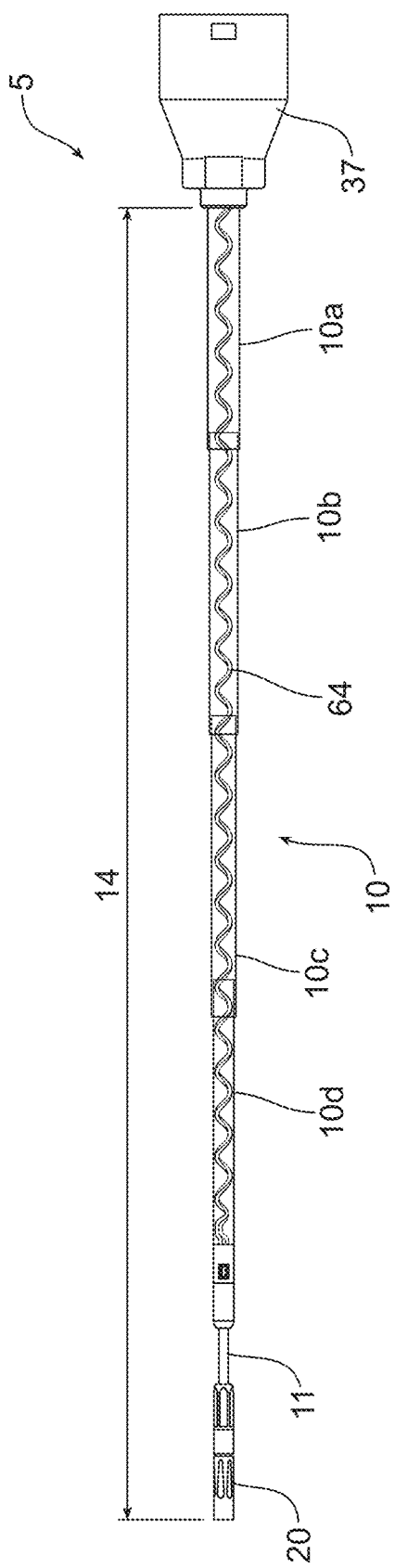

Referring to FIG. 8, a side cross-sectional view of an embodiment of the present invention is shown, with a portion of applicator system 5 shown, including manifold housing 37, cannula 10, and spray and mixing nozzle 20. Applicator system 5 is shown with cannula 10 in extended (elongated) state, with telescopically axially extended cannula 10 having extended length 14. Also shown is the detail of telescopic hollow cannula 10, which comprises of a plurality of hollow tubular segments, four as shown, tubes 10a, 10b, 10c, 10d slidably inserted into one another, and slidably extended, with the coil 64 inside hollow cannula 10 also extended to accommodate elongated state of cannula 10. Coil 64 is sized to fit inside all hollow tubular segments in both extended and non-extended state, particularly to fit inside the smallest tubular segment 10d. Inner tubular segments are configured to not fully separate from their corresponding outer segments, with at least a portion of inner segment always being inside the corresponding outer segment. In some embodiments, at least 3% or 5%, such as least 10% of the inner segment length is always inside the corresponding outer segment, maintaining overall telescoping tubular shape of cannula 10.

Figure 9:
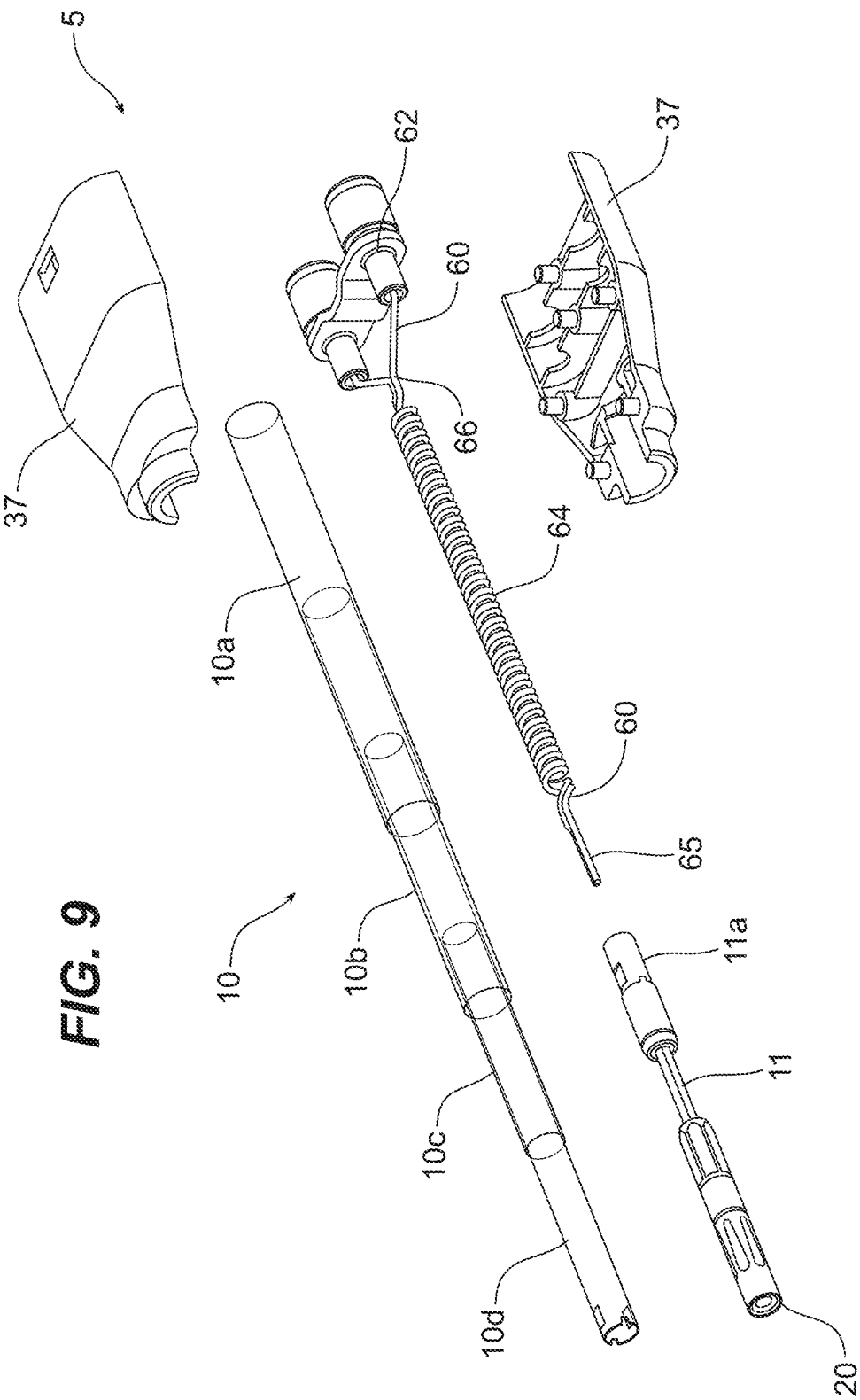

Referring to FIG. 9, a perspective exploded view of an embodiment of the present invention is shown, with a portion of applicator system 5 shown, including manifold housing 37, cannula 10, and spray and mixing nozzle 20. Applicator system 5 is shown with cannula 10 in extended (elongated) state. Also shown is the detail of telescopic hollow cannula 10, which comprises of a plurality of hollow tubes, four as shown, tubes 10a, 10b, 10c, 10d slidably inserted into one another, and slidably extended. Also shown is fitting 11a, configured for connecting coil 64 to connector 11 and to spray and mixing nozzle 20. Coil 64 can have optional non-coiled proximal connecting ends 66 and non-coiled distal connecting ends 65, for connecting to exit connectors 62, fitting 11a and/or connector 11 and spray nozzle 20.

Advantageously, as seen from FIGS. 6-9, in both extended and contracted state of applicator system 5, component tubes 60 comprising coil 64 are still connected to exits 62 of dual barrel syringe 32 and to spray and mixing nozzle 20, thus enabling pumping of liquids from liquid sealant pump 30 or dual barrel syringe 32 into spray nozzle, spray exit port, spray mixing tip, or spray and mixing nozzle 20 and subsequent expression of liquids from nozzle 20.

Figure 10:
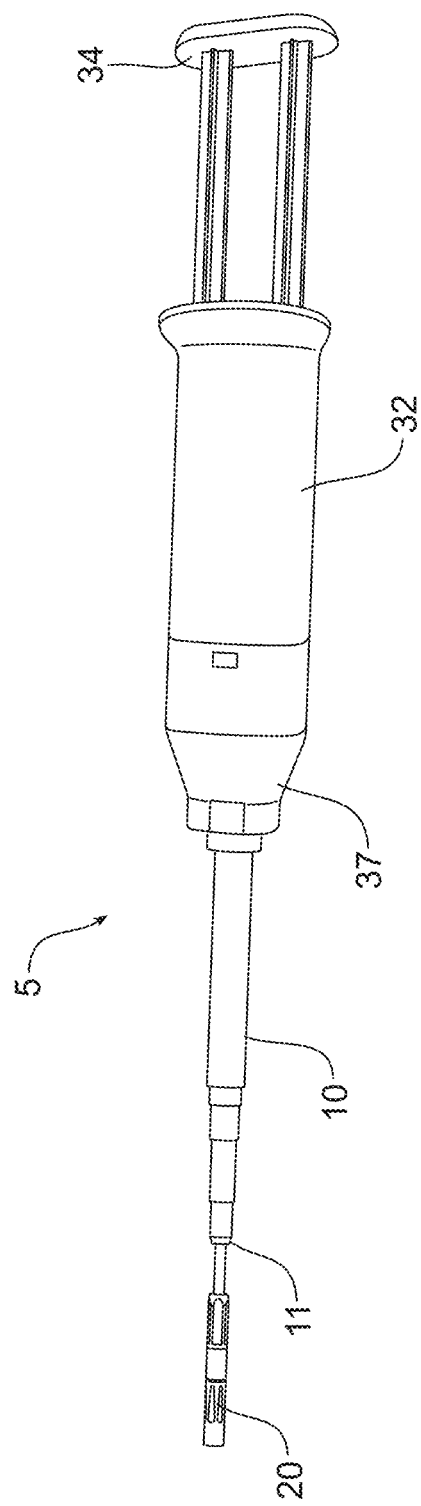
Figure 11:
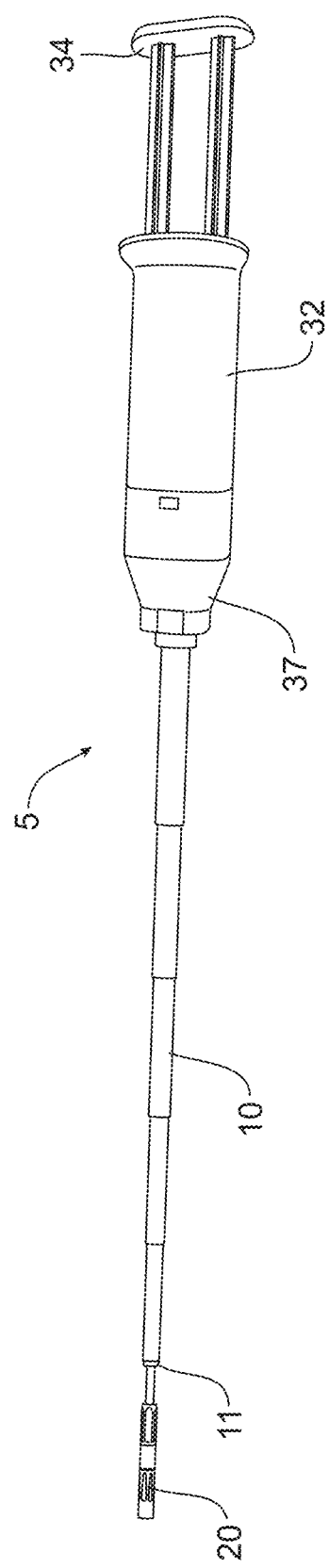

Referring to FIG. 10, a photograph of a side view of an embodiment of the present invention is shown, with applicator system 5 shown with cannula 10 in a non-extended (contracted) state. Referring to FIG. 11, a photograph of a side view of an embodiment of the present invention is shown, with applicator system 5 shown with cannula 10 in extended (elongated) state.

In some embodiments, there is a friction fit between plurality of hollow tubes 10a-10d, to prevent inadvertent contraction of cannula 10 under the contraction spring force of extended coil 64 or upon nozzle 20 inadvertently touching instruments or tissue. In some embodiments, there is a spring-enabled click tabs or click position fixators to reversibly fixate extension of each hollow tube by clicking in place upon extension. In some embodiments, there are internal flanges or internal stop tabs (not shown) that prevent inner tubes from fully separating from outer tubes and forming a break in cannula 10. In some embodiments, there are 2, 3, 4, 5, 6, 7, 8, 9, 10 segments that comprise cannula 10. In some embodiments, segments comprising cannula 10 are of the same or similar length. In some embodiments, segments comprising cannula 10 are of different lengths. In some embodiments, segments having larger diameter are longer, and segments having smaller diameter are shorter.

In some embodiments, there are visible alphanumeric designators or non-alphanumeric markers on hollow tubes or segments comprising cannula 10, indicating to the user the extended length 14 of the extended cannula 10, so that the user can extend cannula 10 to any intermediate length by extending only one segment or inner tube, two, three, or more inner tubes, or to a maximum extended length, when all segments or inner tubes are fully extended. In some embodiments, hollow tubes or segments comprising cannula 10, are color coded, indicating to the user the extended length 14 of the extended cannula 10, so that the user can extend cannula 10 to any intermediate length by extending only one segment or inner tube, two, or more inner tubes, or to a maximum extended length, when all segments or inner tubes are fully extended.

In operation, depressing handle 35 and advancing plungers 34 inside barrels 33 results in liquids being expressed into and sprayed from nozzle 20. Liquid sealant or hemostat advances from syringe barrels 33 into exit connectors 62 and into component tubes 60, flowing through coil 64 into nozzle 20. In operation, axially pulling nozzle 20 or the most distal tubular segment such as 10d, in the direction away from syringe 32 results in telescopic extension of cannula 10 and corresponding matching extension of coil 64 inside cannula 10. In operation, axially pushing nozzle 20 or the most distal tubular segment such as 10d in the direction towards syringe 32 results in telescopic contraction or shortening of cannula 10 and corresponding contraction of coil 64 inside cannula 10. Thus as cannula 10 is elongating/extending, coil 64 follows, extending its length correspondingly or to matching length or to identical length.

In embodiments, an axial telescopic extension or contraction of cannula 10 causes substantially no constricting or kinking of coiled conduit 64 and causes no obstacle to a liquid flow inside coiled conduit 64.

Cannula 10 is telescopically or axially extendable along its main axis to be at least 1.5 times longer in extended state relative to the non-extended state, such as at least 1.5 times, 2 times, 2.5 times, 3 times, 4 times, 5 times longer or more relative to the non-extended state.

Advantageously, in embodiments, coil 64 establishes a direct connection from the syringe to the nozzle 20.

In some embodiments, coil 64 can comprise one, two, three, or more tubes, depending on the number of components and or diluents used.

Figure 12:
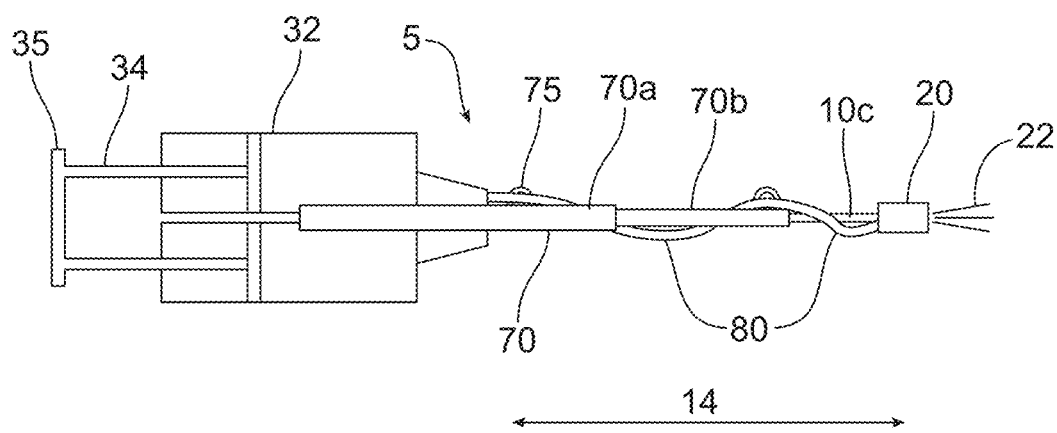
FIG. 12 shows a schematic side cross-sectional view of an embodiment of delivery device or applicator system of the present invention.

Referring to FIG. 12, a schematic side cross-sectional view of delivery device or applicator system 5 is presented in an alternative embodiment. Applicator system 5 is shown with cannula 70 in the extended (elongated) state, with telescopically axially extended cannula 70 having extended length 14. Dual lumen coil 80 is positioned outside of telescopically extendable cannula 70, and is optionally secured to cannula 70 by optional retainers 75. In a preferred embodiment, external coil 80 is wrapped around cannula 70. Cannula 70 is shown to comprise 3 segments, 70a, 70b, 70c, with all segments generally hollow (not shown) to accommodate positioning of smaller segments inside larger segments, similar to cannula 10. In one embodiment, the smallest diameter segment 70c can be a solid rod segment and not hollow. As shown and similar to the embodiments shown supra, dual lumen coil 80 is connecting barrels of dual barrel syringe 32 to nozzle 20 to generate spray 22.

Figure 13:
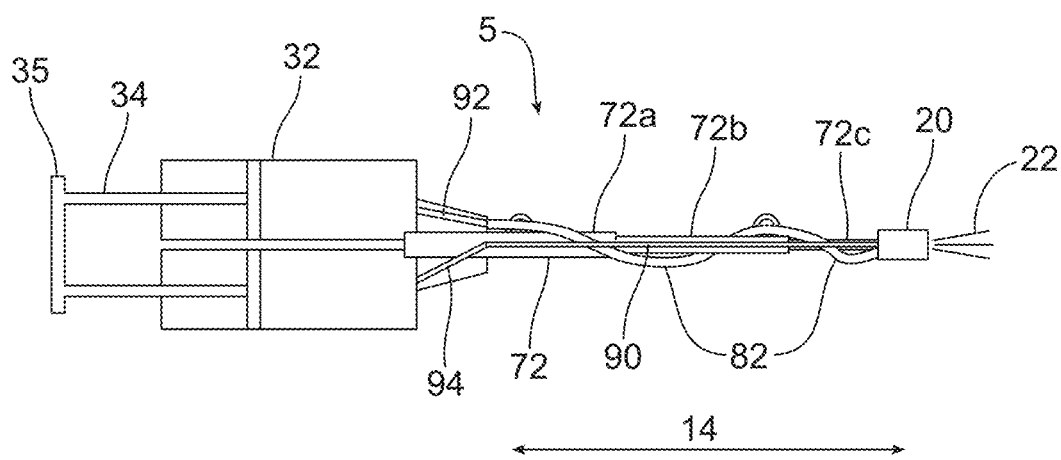
FIG. 13 shows a schematic side cross-sectional view of an embodiment of delivery device or applicator system of the present invention.

Referring to FIG. 13, a schematic side cross-sectional view of delivery device or applicator system 5 is presented in an alternative embodiment. Applicator system 5 is shown with cannula 72 in extended (elongated) state, with telescopically axially extended cannula 72 having extended length 14. Single lumen coil 82 is positioned outside of telescopically extendable hollow cannula 72. In a preferred embodiment, external coil 82 is wrapped around cannula 72. Cannula 72 is shown to comprise 3 segments, 72a, 72b, 72c, with all segments hollow to accommodate positioning of smaller segments inside larger segments, similar to cannula 10. While single lumen coil 82 is in fluid communication with one barrel of syringe 32 via connector 92, and conveys components contained is that one barrel to nozzle 20, the second barrel of syringe 32 is connected via connector 94 to channel 90 inside hollow cannula 72, with the channel terminating at nozzle 20. The components from the second barrel of syringe 32 are conveyed to nozzle 20 via channel 90 inside hollow cannula 72. In this embodiment, the first component is conveyed to nozzle 20 via extendable coiled tube 82 from the first barrel, and the second component is conveyed to nozzle 20 via channel 90 inside telescopically extendable cannula 72 from the second barrel.

Figure 14:
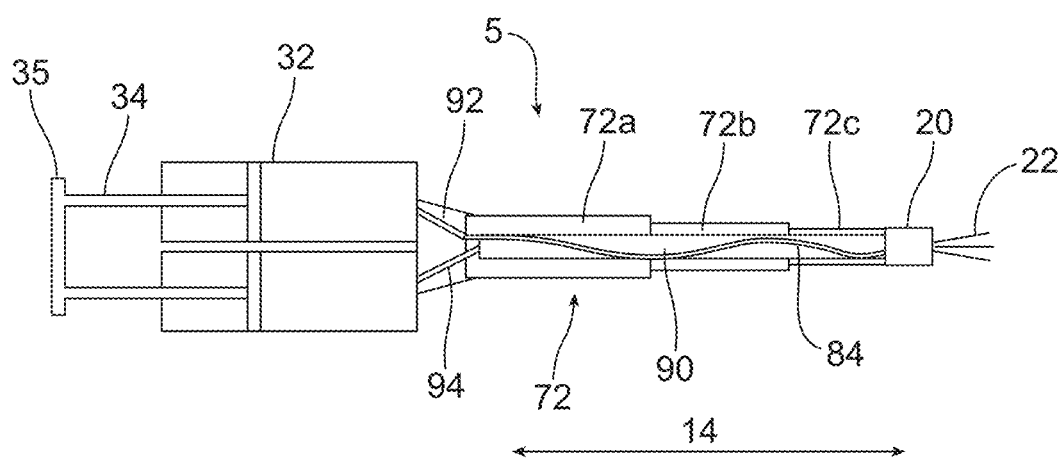
FIG. 14 shows a schematic side cross-sectional view of an embodiment of delivery device or applicator system of the present invention.

Referring to FIG. 14, an embodiment similar to one shown in FIG. 13 is presented. Applicator system 5 is shown with cannula 72 in extended (elongated) state, with telescopically axially extended cannula 72 having extended length 14. In this embodiment, delivery device or applicator system 5 also has single lumen coil 84, but coil 84 is positioned inside of telescopically extendable hollow cannula 72. Cannula 72 is shown to comprise 3 segments, 72a, 72b, 72c, with all segments hollow to accommodate positioning of smaller segments inside larger segments, similar to cannula 10. While single lumen internal coil 84 is in fluid communication with one barrel of syringe 32 via connector 92, and conveys components contained is that one barrel to nozzle 20, the second barrel of syringe 32 is connected via connector 94 to channel 90 inside hollow cannula 72, with the channel terminating at nozzle 20. The components from the second barrel of syringe 32 are conveyed to nozzle 20 via channel 90 inside hollow cannula 72. In this embodiment, first component is conveyed to nozzle 20 via extendable internal coiled tube 84, and the second component is conveyed to nozzle 20 via channel 90 inside telescopically extendable cannula 72.

Materials of construction of the applicator system 5 are any biocompatible materials known to a skilled artisan, including, polymers, composites, glass, metal, and combinations thereof.

In embodiments, dual barrel syringe 32 contains a first liquid in a first barrel and a second liquid in a second barrel, the first and second liquids contain respectively a first and a second reagent, that are reactive upon mixing. Sealant and/or hemostat materials that are expressed from applicator system 5 can be absorbable, not absorbable, and partially absorbable. Sealant and/or hemostat liquids can comprise a one-part composition, with only one liquid 33 to be expressed from pump 30 onto tissue 50. More preferably, sealant or hemostat material can comprise a two-part reactive composition, with two liquid components expressed from pump 30 or from dual barrel syringe 32, with both liquid components either mixing inside nozzle 20, or expressed from nozzle 20 without mixing. The liquid can comprise a medicant, a sealant, a hemostatic compound, a diluent, a rapidly curable or rapidly cross-linkable composition, and combinations thereof. In some embodiments, two-part liquid components are reactive with each other. In some embodiments, at least one of two-part composition components is reactive with blood, tissue, or both.

In one embodiment, the liquid used is one of cyanoacrylates (2-butyl cyanoacrylate, 2-octyl cyanoacrylate), or other synthetic polymers (polyurethanes, polymethylmethacrylates), or multi-arm PEG-SG (succinimidyl glutarate ester) or PEG-NETS. In one embodiment, two liquid components used are solutions of fibrinogen and thrombin. In one embodiment, the liquids used are multi-arm reactive polyethylene glycol polymers having at least 2, more preferably 3, 4, or more reactive groups, such as electrophilic and/or nucleophilic groups. In one embodiment, one of the liquids comprises or multi-arm PEG-SG (succinimidyl glutarate ester) or PEG-NETS or N-Hydroxysuccinimide. The second liquid comprises PEG-amine, albumin, or any amine containing protein solution. In some embodiments, liquids further comprise buffers, diluents, colorants, and combinations thereof.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. The scope of the present invention should be considered in terms of the following claims and is understood not to be limited to the details of structure and operation shown and described in the specification and drawings.

We claim:

1. A variable length applicator system for delivery of at least one medically useful liquid, comprising:
   a) an elongated, telescopically extendable, variable length cannula having a liquid pump containing said liquid connected to said cannula at a proximal end, and a spray nozzle mounted on said cannula at a distal end;
   b) a coiled and extendable tubular conduit connected to and in fluid communication with, both said liquid pump and said spray nozzle;
      1) wherein an axial extension of said cannula is configured to cause a matching axial extension of said coiled tubular conduit,
      2) wherein said pump comprises a dual barrel syringe containing a first liquid in a first barrel and a second liquid in a second barrel,
      3) wherein said first and second liquids contain respectively a first and a second reagent, wherein said reagents are reactive upon mixing, and
      4) wherein said coiled conduit comprises a dual lumen coil.

2. The applicator system of claim 1, wherein said spray nozzle comprises a mixing nozzle.

3. The applicator system of claim 2, wherein said coiled conduit further has non-coiled ends connected to said liquid pump and said spray nozzle.

4. The applicator system of claim 1, wherein said cannula is hollow and said coiled conduit is positioned inside said cannula.

5. The applicator system of claim 4, wherein said cannula comprises a plurality of hollow tubular segments that are axially aligned and slidably inserted into one another, forming outer and inner segments,
   with cannula configured to slidably extend axially telescopically when inner segments are axially pulled from outer segments and to slidably contract axially telescopically when said inner segments axially slide back into said outer segments.

6. The applicator system of claim 5, wherein said coiled conduit is sized to fit into a segment of said cannula having a smallest internal diameter.

7. The applicator system of claim 6, wherein an axial telescopic extension or contraction of said cannula causes substantially no constricting or kinking of said coiled conduit and causes no obstacle to a liquid flow inside said coiled conduit.

8. The applicator system of claim 1, wherein the liquid is selected from the group consisting of a hemostatic material, a sealant material, a rapidly crosslinkable material, a rapidly curable material, and combinations thereof.

9. The applicator system of claim 1, wherein said first liquid comprises a compound having nucleophile groups and said second liquid comprises a compound having electrophile groups.

10. The applicator system of claim 9, wherein nucleophile group comprise amine groups, and said compound having electrophile groups comprises multi-arm polyethylene glycol with NHS groups (PEG-NHS).

11. A variable length applicator system for delivery of at least one medically useful liquid, comprising:
   a) an elongated, telescopically extendable, variable length cannula having a liquid pump containing said liquid connected to said cannula at a proximal end, and a spray nozzle mounted on said cannula at a distal end;
   b) a coiled and extendable tubular conduit connected to and in fluid communication with, both said liquid pump and said spray nozzle;
      1) wherein an axial extension of said cannula is configured to cause a matching axial extension of said coiled tubular conduit,
      2) wherein said pump comprises a dual barrel syringe containing a first liquid in a first barrel and a second liquid in a second barrel,
      3) wherein said first and second liquids contain respectively a first and a second reagent, wherein said reagents are reactive upon mixing, and
      4) wherein said coiled conduit is positioned outside said cannula and is wrapped around said cannula.

12. The applicator system of claim 11, wherein said coiled conduit comprises a dual lumen coil.

13. The applicator system of claim 11, wherein said coiled conduit comprises a single lumen coil.

14. The applicator system of claim 13, wherein
   a) said single lumen coil is in fluid communication with said first barrel and configured to convey said first liquid to said spray nozzle;
   b) said second barrel is in fluid communication with a channel inside said cannula, and
   c) said channel is connected to said spray nozzle and conveys said second liquid to said spray nozzle.

15. A variable length applicator system for delivery of at least one medically useful liquid, comprising:
   a) an elongated, telescopically extendable, variable length cannula having a liquid pump containing said liquid connected to said cannula at a proximal end, and a spray nozzle mounted on said cannula at a distal end;
   b) a coiled and extendable tubular conduit connected to and in fluid communication with, both said liquid pump and said spray nozzle;
   wherein an axial extension of said cannula is configured to cause a matching axial extension of said coiled tubular conduit,
      1) wherein said pump comprises a dual barrel syringe containing a first liquid in a first barrel and a second liquid in a second barrel,
      2) wherein said first and second liquids contain respectively a first and a second reagent, wherein said reagents are reactive upon mixing,
      3) wherein
         (i) said coiled conduit comprises a single lumen coil that is positioned inside a channel in said cannula,
         (ii) said single lumen coil is in fluid communication with said first barrel and configured to convey said first liquid to said spray nozzle;
         (iii) said second barrel is in fluid communication with said channel inside said cannula, and
         (iv) said channel is connected to said spray nozzle and configured to convey said second liquid to said spray nozzle.

16. A method of using the applicator system of claim 1, comprising the steps of:
   a) Directing said spray nozzle towards a target;
   b) Telescopically extending or contracting said cannula towards said target or from said target until an optimal spraying distance between said target and said spray nozzle is reached;
   c) Actuating said liquid pump causing expression of said liquid onto said target;
wherein step (i) can be performed before or after step (ii).

17. A method of making of the applicator system of claim 1, comprising the steps of:
   a) Positioning the coiled and extendable tubular conduit inside said elongated, telescopically extendable, variable length cannula;
   b) connecting said liquid pump to said cannula at the proximal end,
   c) mounting the spray nozzle on said cannula at the distal end; and
   d) establishing fluid communication with between said liquid pump and said spray nozzle through said coiled and extendable tubular conduit.

18. A method of treating an animal tissue using the applicator system of claim 1, comprising:
   a) Directing said spray nozzle towards the tissue prior to or after telescopically extending or contracting said cannula towards the tissue or from the tissue until an optimal spraying distance between the tissue and the spray nozzle is reached;
   b) Actuating the liquid pump causing expression of the liquid onto the tissue; and
   c) Coating the tissue with the liquid.

* * * * *